United States Patent
Cox et al.

(10) Patent No.: US 7,864,326 B2
(45) Date of Patent: Jan. 4, 2011

(54) COMPACT GAS SENSOR USING HIGH REFLECTANCE TERAHERTZ MIRROR AND RELATED SYSTEM AND METHOD

(75) Inventors: James Allen Cox, New Brighton, MN (US); Barrett E. Cole, Bloomington, MN (US)

(73) Assignee: Honeywell International Inc., Morristown, NJ (US)

( * ) Notice: Subject to any disclaimer, the term of this patent is extended or adjusted under 35 U.S.C. 154(b) by 35 days.

(21) Appl. No.: 12/261,823

(22) Filed: Oct. 30, 2008

(65) Prior Publication Data

US 2010/0110447 A1 May 6, 2010

(51) Int. Cl.
*G01B 9/02* (2006.01)
(52) U.S. Cl. .................................. 356/454; 356/519
(58) Field of Classification Search ................. 356/454, 356/480, 506, 519
See application file for complete search history.

(56) References Cited

U.S. PATENT DOCUMENTS

| | | | |
|---|---|---|---|
| 4,233,568 A | 11/1980 | Hamerdinger et al. |
| 4,612,647 A | 9/1986 | Norvell |
| 4,614,961 A | 9/1986 | Khan et al. |
| 4,672,624 A | 6/1987 | Ford |
| 4,870,224 A | 9/1989 | Smith et al. |
| 4,973,131 A | 11/1990 | Carnes |
| 5,022,745 A | 6/1991 | Zayhowski et al. |
| 5,040,895 A | 8/1991 | Laurent et al. |
| 5,135,304 A | 8/1992 | Miles et al. |
| 5,146,465 A | 9/1992 | Khan et al. |
| 5,278,435 A | 1/1994 | Van Hove et al. |
| 5,408,319 A | 4/1995 | Halbout et al. |
| 5,418,868 A | 5/1995 | Cohen et al. |
| 5,450,053 A | 9/1995 | Wood |

(Continued)

FOREIGN PATENT DOCUMENTS

DE 3311808 10/1984

(Continued)

OTHER PUBLICATIONS

W. Henderson, et al., "Resonant Measurement Techniques Using Backward Wave Oscillators", Part of the 4th International Conference on Millimeter and Submillimeter Waves and Applications, San Diego, Jul. 1998, SPIE vol. 3465, p. 218-226.

(Continued)

*Primary Examiner*—Hwa S. A Lee
(74) *Attorney, Agent, or Firm*—Munck Carter, LLP

(57) ABSTRACT

A system and method includes a tunable light source and a gas cell configured to detect the presence of gases at terahertz frequencies. The light source is operable to emit a light signal at terahertz frequencies. The gas cell includes at least two high frequency mirrors adapted to reflect signals at terahertz frequencies. The gas cell is adapted to be tuned based on the frequency of the emitted light to obtain a Fabry-Perot resonance of the reflected light signal. A pair of detectors are operable to detect the original light signal and the light signal reflected through absorption paths in the gas cell. The system and method are operable to determine a presence and identity of a gas present in the gas cell.

21 Claims, 10 Drawing Sheets

U.S. PATENT DOCUMENTS

| | | |
|---|---|---|
| 5,468,910 A | 11/1995 | Knapp et al. |
| 5,512,750 A | 4/1996 | Yanka et al. |
| 5,528,040 A | 6/1996 | Lehmann |
| 5,550,373 A | 8/1996 | Cole et al. |
| 5,629,951 A | 5/1997 | Chang-Hasnain et al. |
| 5,677,538 A | 10/1997 | Moustakas et al. |
| 5,679,965 A | 10/1997 | Schetzina |
| 5,723,706 A | 3/1998 | Brasier et al. |
| 5,739,554 A | 4/1998 | Edmond et al. |
| 5,815,277 A | 9/1998 | Zare et al. |
| 5,834,331 A | 11/1998 | Razeghi |
| 5,835,231 A | 11/1998 | Pipino |
| 5,847,397 A | 12/1998 | Moustakas |
| 5,869,896 A | 2/1999 | Baker et al. |
| 5,900,650 A | 5/1999 | Nitta |
| 5,909,280 A | 6/1999 | Zavracky |
| 5,912,740 A | 6/1999 | Zare et al. |
| 5,915,051 A | 6/1999 | Damask et al. |
| 5,933,565 A | 8/1999 | Diebold |
| 5,960,025 A | 9/1999 | Thorland et al. |
| 6,040,895 A | 3/2000 | Haas |
| 6,080,988 A | 6/2000 | Ishizuya et al. |
| 6,084,682 A | 7/2000 | Zare et al. |
| 6,091,504 A | 7/2000 | Walker et al. |
| 6,094,267 A | 7/2000 | Levenson et al. |
| 6,115,122 A | 9/2000 | Bao et al. |
| 6,122,416 A | 9/2000 | Ooba et al. |
| 6,147,756 A | 11/2000 | Zavracky et al. |
| 6,208,798 B1 | 3/2001 | Morozov et al. |
| 6,233,052 B1 | 5/2001 | Zare et al. |
| 6,287,940 B1 | 9/2001 | Cole et al. |
| 6,295,130 B1 | 9/2001 | Sun et al. |
| 6,296,779 B1 | 10/2001 | Clark et al. |
| 6,310,904 B1 | 10/2001 | Thorland et al. |
| 6,324,192 B1 | 11/2001 | Tayebati |
| 6,335,669 B1 | 1/2002 | Miyazaki et al. |
| 6,377,350 B1 | 4/2002 | Paldus et al. |
| 6,380,531 B1 | 4/2002 | Sugihwo et al. |
| 6,384,953 B1 | 5/2002 | Russell et al. |
| 6,404,648 B1 | 6/2002 | Slupe et al. |
| 6,406,578 B1 | 6/2002 | Schober et al. |
| 6,421,127 B1 | 7/2002 | McAndrew et al. |
| 6,424,419 B1 | 7/2002 | Tazartes et al. |
| 6,438,149 B1 | 8/2002 | Tayebati et al. |
| 6,452,680 B1 | 9/2002 | Paldus et al. |
| 6,466,322 B1 | 10/2002 | Paldus et al. |
| 6,483,130 B1 | 11/2002 | Yang et al. |
| 6,492,726 B1 | 12/2002 | Quek et al. |
| 6,507,107 B2 | 1/2003 | Vaiyapuri |
| 6,532,071 B2 | 3/2003 | Zare et al. |
| 6,545,739 B1 | 4/2003 | Matsumoto et al. |
| 6,583,917 B2 | 6/2003 | Melloni et al. |
| 6,584,126 B2 | 6/2003 | Wang et al. |
| 6,590,710 B2 | 7/2003 | Hara et al. |
| 6,594,059 B2 | 7/2003 | Flanders |
| 6,597,713 B2 | 7/2003 | Ouchi |
| 6,608,711 B2 | 8/2003 | Flanders et al. |
| 6,627,983 B2 | 9/2003 | Tu et al. |
| 6,658,034 B2 | 12/2003 | Garnache et al. |
| 6,670,559 B2 | 12/2003 | Centola et al. |
| 6,728,286 B2 | 4/2004 | Thorland et al. |
| 6,784,946 B1 | 8/2004 | Schroter et al. |
| 6,836,501 B2 | 12/2004 | Cox et al. |
| 6,879,014 B2 | 4/2005 | Wagner et al. |
| 6,947,218 B2 * | 9/2005 | Turner, III .................. 359/589 |
| 6,985,281 B2 | 1/2006 | Wagner et al. |
| 7,002,697 B2 | 2/2006 | Domash et al. |
| 7,012,696 B2 | 3/2006 | Orr et al. |
| 7,015,457 B2 | 3/2006 | Cole et al. |
| 7,046,326 B2 | 5/2006 | Austin et al. |
| 7,049,004 B2 | 5/2006 | Domash et al. |
| 7,050,170 B2 | 5/2006 | Chilese et al. |
| 7,089,781 B2 | 8/2006 | Petrovic et al. |
| 7,106,763 B2 | 9/2006 | Tan et al. |
| 7,113,256 B2 | 9/2006 | Butler et al. |
| 7,145,165 B2 | 12/2006 | Cox et al. |
| 7,147,165 B2 | 12/2006 | Mongin et al. |
| 7,147,695 B2 | 12/2006 | Mitra |
| 7,221,827 B2 | 5/2007 | Domash et al. |
| 7,259,856 B2 | 8/2007 | Kachanov et al. |
| 7,304,799 B2 | 12/2007 | Ma et al. |
| 7,352,463 B2 | 4/2008 | Bounaix |
| 7,612,885 B2 * | 11/2009 | Cole et al. .................. 356/437 |
| 2002/0191268 A1 | 12/2002 | Seeser et al. |
| 2003/0107739 A1 | 6/2003 | Lehmann et al. |
| 2003/0173499 A1 | 9/2003 | Cole et al. |
| 2003/0210398 A1 | 11/2003 | Augustine et al. |
| 2004/0107764 A1 | 6/2004 | Yan |
| 2004/0194628 A1 | 10/2004 | Mitra |
| 2004/0217264 A1 | 11/2004 | Wood et al. |
| 2004/0234198 A1 | 11/2004 | Wagner et al. |
| 2004/0255853 A1 | 12/2004 | Ma et al. |
| 2005/0030628 A1 | 2/2005 | Wagner et al. |
| 2005/0040337 A1 | 2/2005 | Cox et al. |
| 2005/0052653 A1 | 3/2005 | Fidric |
| 2005/0062972 A1 | 3/2005 | Krusen |
| 2005/0082480 A1 | 4/2005 | Wagner et al. |
| 2005/0094158 A1 | 5/2005 | Paldus et al. |
| 2005/0105184 A1 | 5/2005 | Ma et al. |
| 2005/0122520 A1 | 6/2005 | Yan |
| 2005/0122523 A1 | 6/2005 | Yan |
| 2005/0134836 A1 | 6/2005 | Paldus et al. |
| 2005/0254056 A1 | 11/2005 | Kachanov et al. |
| 2006/0054795 A1 | 3/2006 | Cole et al. |
| 2006/0082778 A1 | 4/2006 | Paldus et al. |
| 2006/0083284 A1 | 4/2006 | Paldus et al. |
| 2006/0084180 A1 | 4/2006 | Paldus et al. |
| 2006/0087655 A1 | 4/2006 | Augustine et al. |
| 2006/0151248 A1 | 7/2006 | Rodriguez et al. |
| 2006/0261252 A1 | 11/2006 | Cole et al. |
| 2007/0133001 A1 | 6/2007 | Cox et al. |
| 2007/0146720 A1 | 6/2007 | Cox et al. |
| 2007/0278407 A1 | 12/2007 | Wood et al. |
| 2008/0074662 A1 | 3/2008 | Gu et al. |
| 2008/0151248 A1 | 6/2008 | Cole et al. |
| 2008/0239299 A1 | 10/2008 | Cole |
| 2009/0014670 A1 | 1/2009 | Cole et al. |

FOREIGN PATENT DOCUMENTS

| | | |
|---|---|---|
| DE | 19635421 | 12/1997 |
| EP | 0 177 918 B1 | 3/1991 |
| EP | 0 667 548 A1 | 8/1995 |
| EP | 1 061 618 A2 | 12/2000 |
| EP | 1 069 658 A1 | 1/2001 |
| EP | 1 070 943 A1 | 1/2001 |
| EP | 1 847 825 A1 | 10/2007 |
| JP | 03-252172 | 11/1991 |
| JP | 05-095130 | 4/1993 |
| JP | 7-288334 A | 10/1995 |
| WO | WO 93/26049 | 12/1993 |
| WO | WO 99/42875 A | 8/1999 |
| WO | WO 02/04903 A1 | 1/2002 |
| WO | WO 03/098173 A1 | 11/2003 |
| WO | WO 2005/108939 A1 | 11/2005 |

OTHER PUBLICATIONS

F. Rutz, et al., "Improved dielectric mirrors for the THz frequency range", Proc. of SPIE vol. 6194 (2006), 9 pages.

Robert Schiwon, et al., "Far-infrared multilayer mirrors", Applied Physics Letters, vol. 83, No. 20, Nov. 17, 2003, p. 4119-4121.

Todd W. Du Bosq, et al., "High reflectivity intracavity Bragg mirrors for the far-infrared p-Ge laser", Proceedings of SPIE vol. 5411, (2004), p. 167-173.

Justin W. Cleary, et al., "Scanning Fabry-Perot filter for terahertz spectroscopy based on silicon dielectric mirrors", Proc. of SPIE vol. 6472, (2007), 12 pages.

Justin W. Cleary, et al., "Finesse of silicon-based terahertz Fabry-Perot spectrometer", Proc. of SPIE vol. 6549, (2007), 7 pages.

Robert Schiwon, et al., "Terahertz cavity-enhanced attenuated total reflection spectroscopy", Applied Physics Letters 86, 201116 (2005), 3 pages.

Andrew C. R. Pipino, et al., "Evanescent wave cavity ring-down spectroscopy with a total-internal-reflection minicavity", Rev. Sci. Instrum. 68 (8), Aug. 1997, p. 2978-2989.

Ralph W. Bernstein, et al., "Development of a Miniature Silicon PhotoAcoustic Gas Sensor", Presented at Opto 96, Leipzig, Germany, Sep. 26-29, 1999, 6 pages.

J.D. Brown, et al., "Visible-Blind UV Digital Camera Based On a 32×32 Array of GaN/AlGaN p-i-n Photodiodes", MRS Internet Journal Nitride Semiconductor Research 4, 9 (1999), 10 pages.

Alain Campargue, et al., "Measurement of $SiH_2$ density in a discharge by intracavity laser absorption spectroscopy and CW cavity ring-down spectroscopy", 1998, p. 1168-1175.

N. Chitica, et al., "Monolithic InP-Based Tunable Filter with 10-nm Bandwidth for Optical Data Interconnects in the 1550-nm Band", IEEE Photonics Technology Letters, vol. 11, No. 5, May 1999, p. 584-586.

Shang-I Chou, et al., "Diode-Laser Measurements of He-, Ar-, and N2-Broadened HF Lineshapes in the First Overtone Band", Journal of Molecular Spectroscopy 196 (1999), p. 70-76.

Seok-Whan Chung, et al., "Design and fabrication of 10×10 microspatial light modulator array for phase and amplitude modulation", Sensors and Actuators 78 (1999), p. 63-70.

B.R. Johnson, et al., "Microscopic Spectroscopy of Optical MEMS Devices", Topic 2 (Materials and Technology), Honeywell Laboratories, around Dec. 11, 2000, 2 pages.

T.H. Edwards, "Multiple-Traverse Absorption Cell Design", Journal of the Optical Society of America, vol. 51., No. 1, Jan. 1961, p. 98-102.

A.M. Ferber, et al., "A Miniature Silicon Photoacoustic Detector For Gas Monitoring Applications", Paper Presented at the mtec 2001 International Conference on Sensors & Transducers, Birmingham, UK, Feb. 14, 2001, 7 pages.

J.H. Jerman, et al., "A miniature Fabry-Perot interferometer with a corrugated silicon diaphragm support", Sensors and Actuators—A Physical A29 Nov. 1991, No. 2, Lausanne, CH, p. 151-158.

V.Yu. Kurochkin, et al., "Complex-cavity two-mode CO2 laser for saturated intracavity absorption", Opt. Spectrosc. (USSR) 68 (6), Jun. 1990, p. 793-797.

V.Yu. Kurochkin, et al., "Three-mirror cavity CO2 laser for intracavity saturated-absorption spectroscopy", Opt. Spectrosc. (USSR) 65 (2), Aug. 1988, p. 265-267.

Anthony O'Keefe, et al., "Cavity ring-down optical spectrometer for absorption measurements using pulsed laser sources", Review of Scientific Instruments, 59, 2544 (1988), 11 pages.

J.B. Paul, et al., "Cavity ringdown measures trace concentrations", Laser Focus World, Mar. 1997, p. 71-80.

Bruce A. Richman, et al., "Continuously tunable, single-longitudinal-mode, pulsed mid-infrared optical parametric oscillator based on periodically poled lithium niobate", 2000 Optical Society of America, vol. 17, No. 7, Jul. 2000, p. 1233-1239.

N. Sadeghi, et al., "Cavity Ring Down Spectroscopy Applied To Plasma Diagnostics", Proc. Int. Symp. Laser-aided Plasma Diagnostics, Lake Tahoe, CA, Sep. 1999, 8 pages.

J.J. Scherer, et al., "Infrared cavity ringdown laser absorption spectroscopy (IR-CRLAS) in low pressure flames", Appl. Phys. B. 64 (1997), p. 699-705.

Bill Schweber, "An Old Communications Problem Reoccurs in Optical-Communication-System Design, How it Works: making the laser diode tunable", EDN, Sep. 28, 2000, p. 44-48.

Fujio Shimizu, et al., "Stark spectroscopy by 10-μ lasers using a multipath cell", Journal of Applied Physics, vol. 46, No. 1, Jan. 1975, p. 258-259.

V.S. Smirnov, "Dye Lasers Using A Three-Mirror Cavity with Lamp Excitation", Zhurnal Prikladnoi Spektroskopii, vol. 34, No. 3, Mar. 1981, p. 275-278.

T.G. Spence, et al., "A laser-locked cavity ring-down spectrometer employing an analog detection scheme", Review of Scientific Instrucments, vol. 61, No. 2, Feb. 2000, p. 347-353.

S.M. Sze, "Physics of Semiconductor Devices", Aug. 20, 1982, 4 pages.

P. Tayebati, et al., "Microelectromechanical tunable filter with stable half symmetric cavity", Electronic Letters Online No. 19981350, Jul. 9, 1998, 2 pages.

P. Tayebati, et al., "Widely Tunable Fabry-Perot Filters using High Index-contrast DBRs", SPIE vol. 3234, 1998, p. 206-208.

Wei Yang, et al., "Back-illuminated GaN/AlGaN heterojunction photodiodes with high quantum efficiency and low noise", Applied Physics Letters, vol. 73, No. 8, Aug. 24, 1998, 5 pages.

James Allen Cox, et al., "High Reflectance Terahertz Mirror and Related Method", U.S. Appl. No. 12/261,911, filed Oct. 30, 2008.

* cited by examiner

COMPACT GAS SENSOR USING HIGH REFLECTANCE TERAHERTZ MIRROR AND RELATED SYSTEM AND METHOD

TECHNICAL FIELD

This disclosure relates generally to wireless devices and more specifically to a compact gas sensor using high reflectance terahertz mirror and related system and method.

BACKGROUND

Gas detectors often utilize infrared detection to detect the presence and concentration of certain gases in a particular area. When a gas is in the presence of infrared light, the gas can absorb some of the infrared light's energy. Specific gases absorb infrared light at specific wavelengths, allowing the identification of gases by measuring the absorption of light at those wavelengths. Optical filters are often used to pass only particular wavelengths for a gas of interest.

Gas detectors frequently incorporate high reflectance mirrors to reflect a light signal within a measuring chamber. A light source emits a light signal, such as infrared light, towards the high reflectance mirror. The high reflectance mirror then reflects the light signal towards a detector (such as an antenna). The detector compares the amount of light transmitted through the sample of gas. The detector can therefore determine the concentration of gas present in the sample by measuring the light that passes through the sample. For example, if the amount of light transmitted through the sample is equal to that of a reference gas, the sample may not contain a gas of interest. Conversely, a measured difference between the amount of light transmitted through the sample and the reference gas can quantitatively determine the concentration of gas in the sample.

A problem with conventional high reflectance mirrors is that they can suffer from significant reflection impairment at higher frequencies. This can be a problem, for example, at frequencies of several hundred gigahertz up into the terahertz range. This reflection impairment can obstruct a proper resonance of the mirror, negatively impacting operation of a gas detector.

SUMMARY

This disclosure provides a compact gas sensor using high reflectance terahertz mirror and related system and method.

In a first embodiment, an apparatus includes a resonant cavity, a light system and a first and second detector devices. The resonant cavity is configured to receive a light signal. The light system includes two or more high reflectance terahertz mirrors. The two or more high reflectance terahertz mirrors are configured to reflect the light signal within the resonant cavity. The light signal is reflected to traverse a number of paths through a gas present in the resonant cavity. The first detector device is configured to measure the received light signal. The second detector is configured to measure the reflected light signal.

In a second embodiment, a system for detecting gases as terahertz frequencies includes a tunable light emission source and a gas cell. The tunable light emission source is configured to emit a light signal at a wavelength in a range between 100 GHz and 10000 GHz. The gas cell includes two or more high reflectance mirrors, a gas resonance cavity, and first and second gas detection devices. The high reflectance mirror is configured to reflect the light signal at a wavelength in a range between 100 GHz and 10,000 GHz. The first gas detection device is configured to detect the emitted light signal. The second gas detection device is configured to detect a reflected light signal from the two or more high reflectance mirrors.

In a third embodiment, a method for detecting gases at terahertz frequencies includes receiving a light signal in a range between 100 GHz and 10,000 Ghz. The light signal is measured by a first detector. Further, the light signal is reflected by at least one high reflectance terahertz mirror. The light signal is reflected towards a detector such that a distance traveled by the light signal is substantially increased. The at least one high reflectance mirror comprises a reflectance greater than 0.999 at a wavelength in a range of 100 GHz and 10,000 Ghz. The reflected light signal is measured by a second detector. The light signal and the reflected light signals are compared to determine an absorption of the light signal. A presence of a gas, corresponding to the absorption of light at a specified frequency, is determined to be present in the gas cell.

Other technical features may be readily apparent to one skilled in the art from the following figures, descriptions, and claims.

BRIEF DESCRIPTION OF THE DRAWINGS

For a more complete understanding of this disclosure, reference is now made to the following description, taken in conjunction with the accompanying drawings, in which.

DETAILED DESCRIPTION

FIGS. 1 through 15, discussed below, and the various embodiments used to describe the principles of the present invention in this patent document are by way of illustration only and should not be construed in any way to limit the scope of the invention. Those skilled in the art will understand that the principles of the invention may be implemented in any type of suitably arranged device or system. Also, it will be understood that elements in the figures are illustrated for simplicity and clarity and have not necessarily been drawn to scale. For example, the dimensions of some elements in the figures may be exaggerated relative to other elements to help improve the understanding of various embodiments described in this patent document.

High reflectance mirrors are often manufactured through thin film manufacturing techniques. For example, thin film manufacturing techniques can produce mirrors formed from stacks of very thin films. These mirrors work very well in the visible and infrared wavelength spectrums. The visible and infrared wavelength spectrums generally have wavelengths with magnitudes between 0.5 microns to 10 microns. Multiple stacks of quarter-wave ("λ/4") layers can be stacked using traditional techniques (such as sputtering) to grow thin films yielding very high quality. However, when the mirrors are required to operate in terahertz ("THz") frequencies, such as where the wavelengths are on the order of 100 microns, the traditional techniques often produce film thickness that are too thick.

Figure 1:
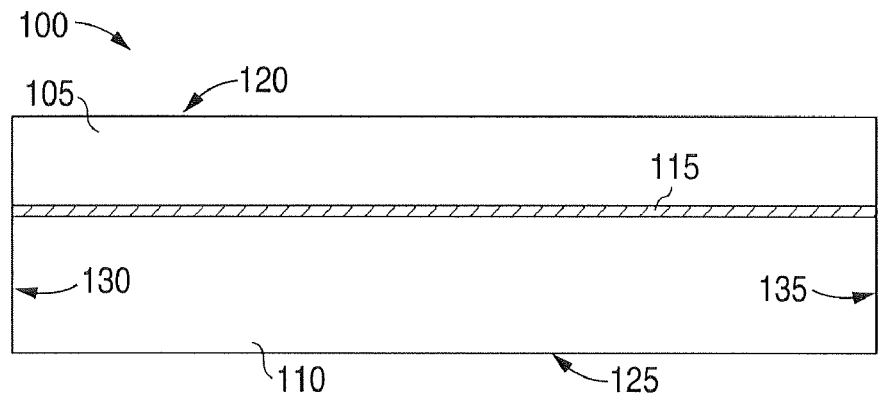
FIG. 1 illustrates an example semiconductor structure according to this disclosure.

FIG. 1 illustrates an example semiconductor structure 100 according to this disclosure. The embodiment of the semiconductor structure 100 shown in FIG. 1 is for illustration only. Other embodiments of the semiconductor structure 100 could be used without departing from the scope of this disclosure.

As described below, the semiconductor structure 100 can be used to form a mirror period to be stacked for use as a high reflectance terahertz reflective mirror. In this example, the semiconductor structure 100 includes a first semiconductor layer 105, which has a higher resistivity value (such as $>10^4$ Ωcm). The first semiconductor layer 105 could be formed from any suitable material(s). In some embodiments, the first semiconductor layer 105 represents a high resistivity silicon wafer, which could have a thickness of approximately 110 μm. The semiconductor layer 105 includes a first side (a top face) and a second side (a bottom face).

The semiconductor structure 100 also includes a second semiconductor layer 110. The second semiconductor layer 110 could be formed from any suitable material(s). Example materials include silicon, gallium arsenide, aluminum antimonide, aluminum arsenide, aluminum nitride, aluminum phosphide, boron nitride, boron phosphide, boron arsenide, gallium antimonide, gallium nitride, gallium phosphide, indium antimonide, indium arsenide, indium nitride, indium phosphide, cadmium zinc telluride, mercury cadmium telluride, mercury zinc telluride, and mercury zinc selenide. In some embodiments, the second semiconductor layer 110 represents a standard single crystal silicon wafer, which could have a thickness of approximately 125 μm. The second semiconductor layer 110 includes a front side (a top face) and a back side (a bottom face).

Silicon on insulator (SOI) wafers are made by growing an oxide layer on a wafer called the handle wafer (e.g., second semiconductor layer 110) fusion bonding the other wafer (e.g., the first semiconductor layer 105) to the handle wafer and then polishing down the handle wafer to the desired thickness. As such, the semiconductor structure 100 can be manufactured by fusion bonding the first semiconductor layer 105 and the second semiconductor layer 110 on an oxide film 115. The oxide film 115 could be approximately 0.5 μm thick. The fusion bonding can be performed so that the oxide film 115 is thermally grown onto the front side of the second semiconductor layer 110. The second side of the first semiconductor layer 105 is fusion bonded on a first face of the oxide film 115. The semiconductor structure 100 itself includes a front side 120, a back side 125, a non-bonding side 130, and a bonding side 135.

Figure 2:
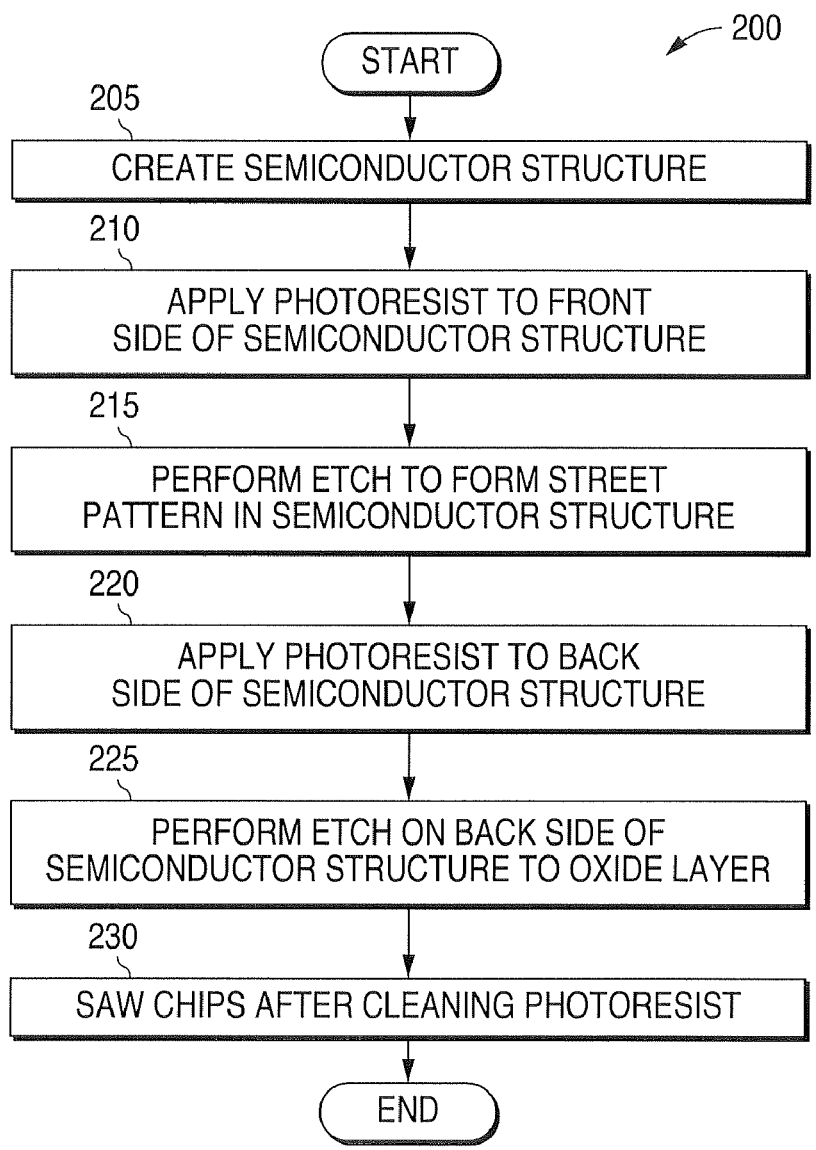
FIG. 2 illustrates an example method for manufacturing a mirror period according to this disclosure.

FIG. 2 illustrates an example method 200 for manufacturing a mirror period according to this disclosure. The embodiment of the method 200 shown in FIG. 2 is for illustration only. Other embodiments of the method 200 could be used without departing from the scope of this disclosure.

As shown in FIG. 2, the method 200 commences at step 205, where the semiconductor structure 100 is manufactured. As noted above, the semiconductor structure 100 can be assembled by fusion bonding a first semiconductor layer 105 and a second semiconductor layer 110 to an oxide film 115.

Figure 3:
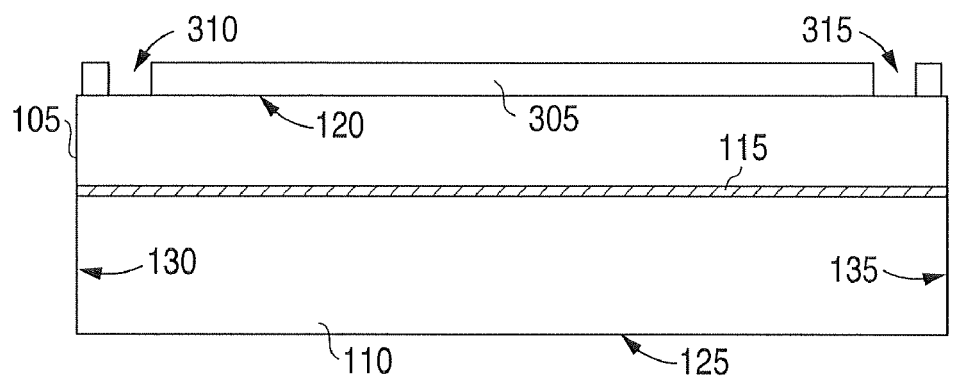
FIGS. 3 through 5, 7, and 8 illustrate an example semiconductor structure at different manufacturing stages according to this disclosure.
Figure 4:
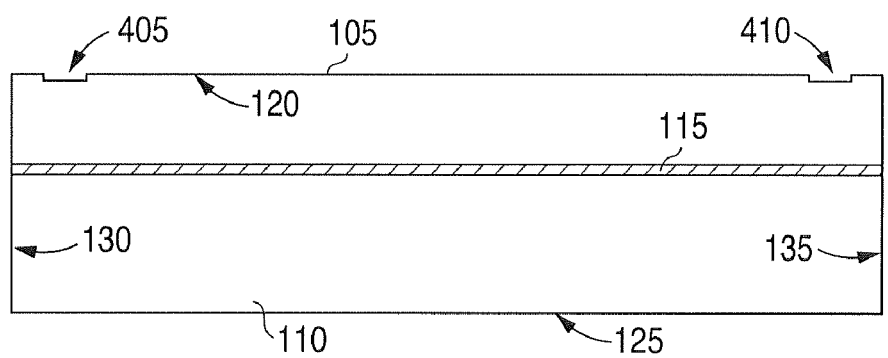

In step 210, a photoresist layer is applied to the front side 120 of the semiconductor structure 100. An example of this is shown in FIG. 3, where a photoresist layer 305 is applied to the front side 120 of the semiconductor structure 100. The photoresist layer 305 includes a pattern having a first via 310 and a second via 315. The first via 310 and the second via 315 can be formed by patterning the photoresist layer 305 using a suitable exposure. The first via 310 and the second via 315 are configured here to delineate cutting streets or sawing guides.

In step 215, an etch is perform to form a street pattern in the front side 120 of the semiconductor structure 100. The etch could represent a very short LAM etch process. The photoresist layer can be removed (such as by stripping) after the etch is performed so that substantially no portion of the photoresist layer remains on the semiconductor structure 100. This produces the structure shown in FIG. 4, where a first street pattern 405 and a second street pattern 410 are formed in the front side 120 of the semiconductor structure 100.

Figure 5:
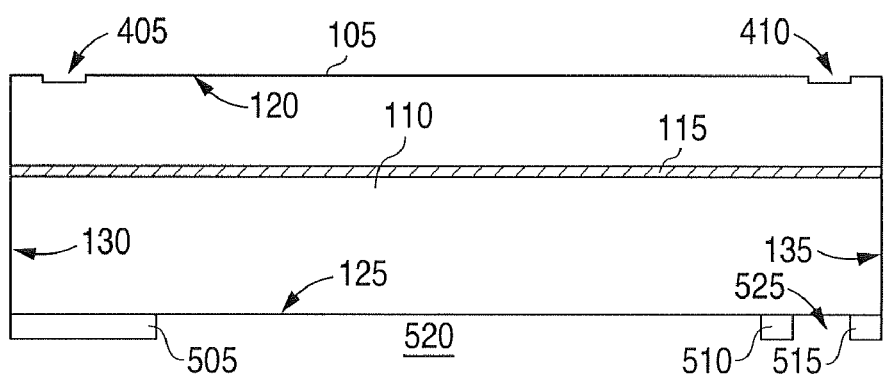

In step 220, a photoresist layer is applied to the back side 125 of the semiconductor structure 100. An example of this is shown in FIG. 5, where a photoresist layer 505, 510 and 515 is applied to the back side 125 of the semiconductor structure 100. The photoresist layer 505, 510 and 515 could be formed in any suitable manner and using any suitable material(s), such as forming a 4,000 Å layer of aluminum using an MA-6 mask aligner. As shown in FIG. 5, the photoresist layer 505, 510 and 515 delineates a window area 520, a glue ledge area 525 and optionally a weep hole (not specifically illustrated) (to allow pressure equilibration between the air chambers after the chips are stacked together). In particular embodiments, the window area 520 can be 1.25 cm to 1.75 cm wide, such as approximately 1.5 cm wide.

Figure 6A:
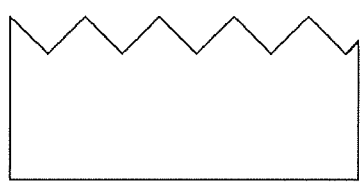
FIGS. 6A and 6B illustrate example etching processes according to this disclosure.
Figure 6B:
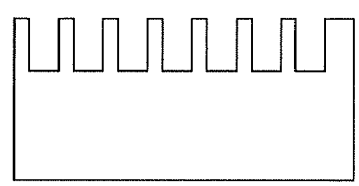
Figure 7:
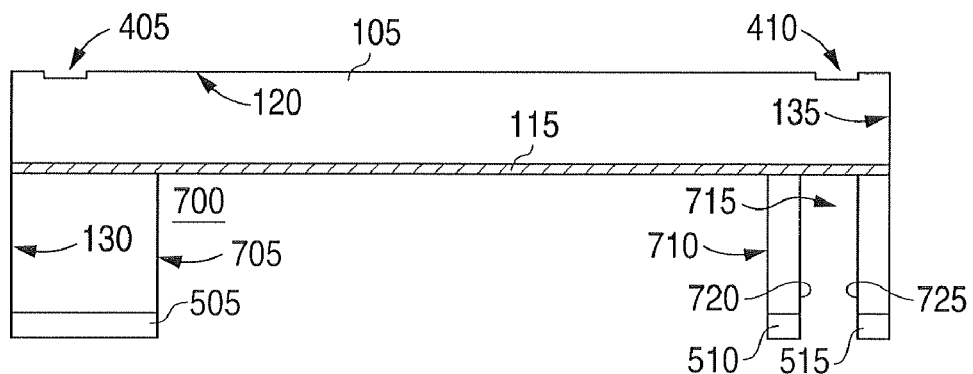

In step 225, an etch is perform on the back side 125 of the semiconductor structure 100 to etch through to the oxide film 115. FIG. 6A illustrates example results produced using a wet etch, while FIG. 6B illustrates example results produced by a deep reactive ion etch ("DRIE"). DRIE is highly anisotropic, while wet etching could yield a profile with 54° (from normal). DRIE etching yields profiles with nearly 90° or perpendicular to the surface. In some embodiments, the etching performed at step 225 is a DRIE etch performed on the back side 125 of the semiconductor structure 100. The results of the etch are shown in FIG. 7, where the DRIE etch has created a notch 700. The notch 700 represents a wide passage to the oxide film 115 through the second semiconductor layer 110. The DRIE etch can naturally terminate at the oxide film 115, helping to increase accuracy and obtain uniform thickness. The notch 700 here is defined by a first sidewall 705 and a second sidewall 710. The notch 700 could be between 1.25 cm to 1.75 cm wide (such as 1.5 cm wide) between its sidewalls. A second notch 715 is also formed in the second semiconductor layer 110 during the DRIE etch. The second notch 715 is defined by a third sidewall 720 and a fourth sidewall 725. Once the etch is complete, the photoresist layer 505, 510 and 515 can be removed (such as by stripping) so that substantially none of the photoresist layer 505, 510 and 515 remains on the semiconductor structure 100.

Figure 8:
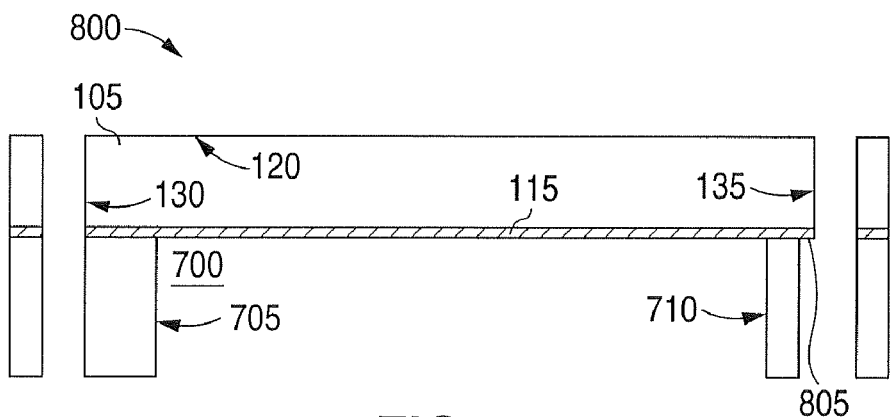

In step 230, the semiconductor structure 100 is diced or cut along the first street pattern 405 and the second street pattern 410. As shown in FIG. 8, cutting along the first street pattern 405 and the second street pattern 410 yields a mirror period 800. Also, a glue ledge 805 is formed on the bonding side 135 of the mirror period 800. The glue ledge 805 may be formed, for example, due to the MA-6 mask aligner aligning the second street pattern 410 with the fourth sidewall 725. This completes the formation of the mirror period 800 as described in FIG. 2.

Figure 9:
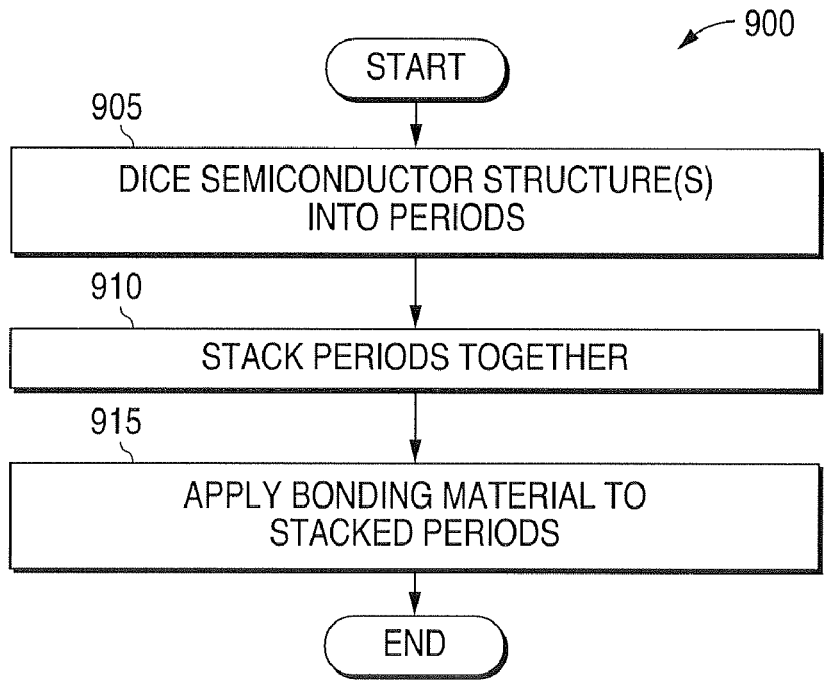
FIG. 9 illustrates an example method for stack bonding mirror periods into a terahertz high reflectance mirror according to this disclosure.

FIG. 9 illustrates an example method 900 for stack bonding mirror periods into a terahertz high reflectance mirror according to this disclosure. The embodiment of the method 900 shown in FIG. 9 is for illustration only. Other embodiments of the method 900 could be used without departing from the scope of this disclosure.

Figure 10:
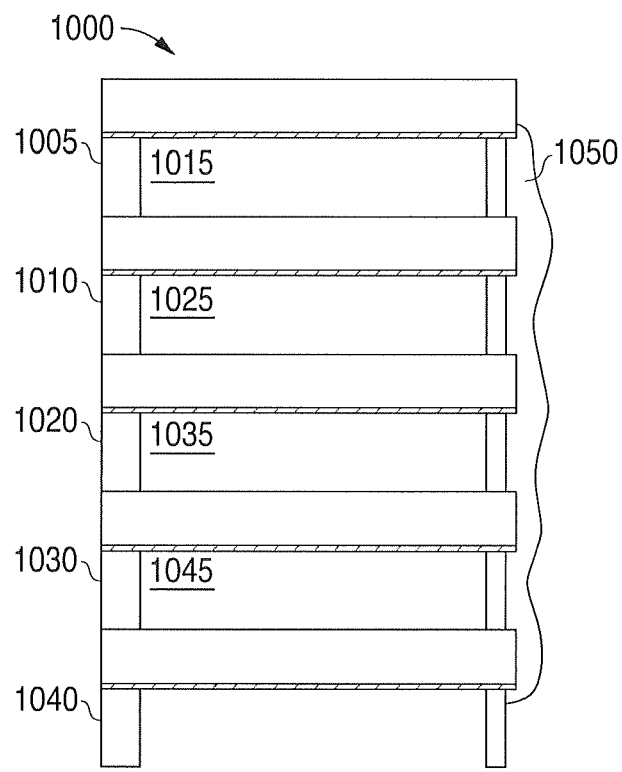
FIG. 10 illustrates an example terahertz high reflectance mirror according to this disclosure.

Multiple periods (such as at least five periods) from one or more semiconductor structure 100 are formed at step 905, such as by using the method 200 of FIG. 2. The periods are then stacked at step 905, an example of which is shown in FIG. 10. As shown in FIG. 10, a first period 1005 is stacked on top of a second period 1010 such that the back side 125 of the first period 1005 is placed adjacent to the front side 120 of the second period 1010. The notch 700 of the first period 1005 and the front side 120 of the second period 1010 form a first period cavity 1015. Similar steps can be used to stack additional periods 1020, 1030, 1040 to form period cavities 1025, 1035, 1045. At step 915, a bonding material 1050 is applied to the stacked periods, forming a completed mirror 1000.

In this example, the mirror 1000 represents a five-period high reflectance terahertz reflective mirror. In particular embodiments, the periods in the mirror 1000 could be formed from high-resistivity (hi-p) silicon and air. The refractive index n of silicon is 3.418 at 300K, and the refractive index for air is "1." Table 1 illustrates the refractive index and optical thickness of high resistivity silicon (Si), silicon dioxide (SiO$_2$), and air.

TABLE 1

|  | Si | | SiO$_2$ | | Air |
| --- | --- | --- | --- | --- | --- |
| OPL | λ/4 | 3λ/4 | λ/4 | 3λ/4 | λ/4 |
| d(μm) | 36.57 | 109.7 | 86.21 | 258.6 | 125 |
| n | 3.418 | | 1.95 + i0.008 | | 1 |

In some embodiments, the first semiconductor layer 105 is between 105 μm and 115 μm thick, and the period cavity is between 120 μm and 130 μm thick. In particular embodiments, the mirror 1000 could include a quarter-wave silicon film and a quarter-wave air design. In these embodiments, the first semiconductor layer 105 in each mirror period can be approximately 37 μm thick, and each period cavity could be 1.5 cm in width and 125 μm in height. In other particular embodiments, the mirror 1000 could include a three-quarter-wave silicon film and a quarter-wave air design. In those embodiments, the first semiconductor layer 105 in each mirror period can be 110 μm thick, and each period cavity could be 1.5 cm in width and 125 μm in height. Here, the thickness tolerances could be less than 10 μm.

Figure 11A:
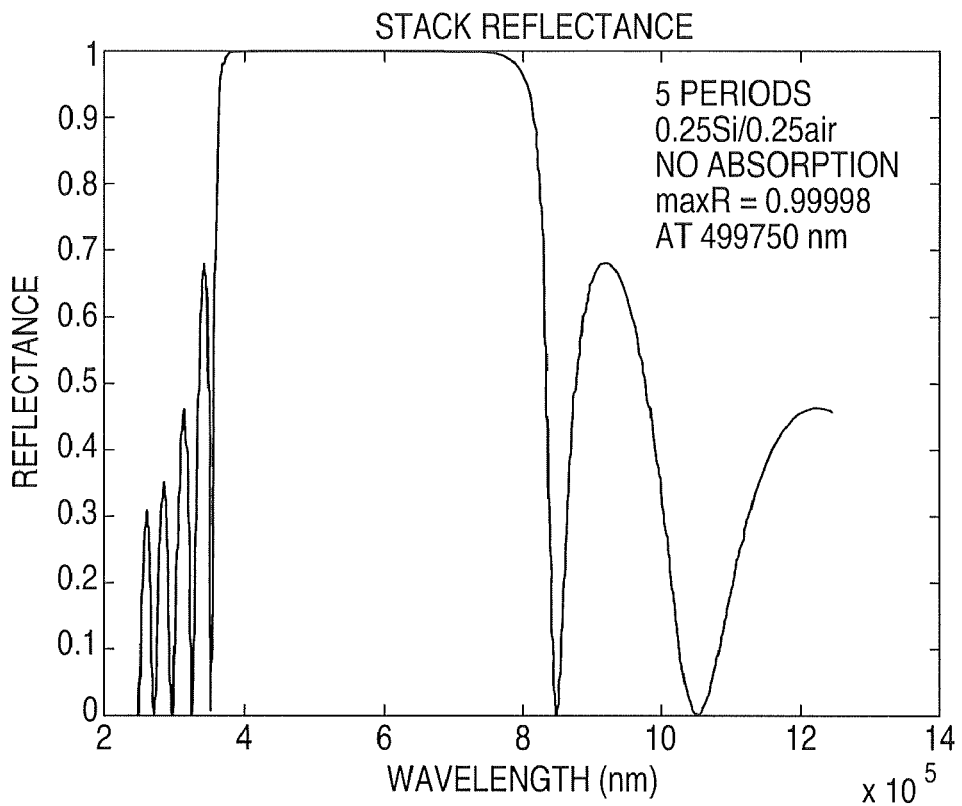
FIGS. 11A and 11B illustrate graphs of example reflectances of a terahertz mirror according to this disclosure.
Figure 11B:
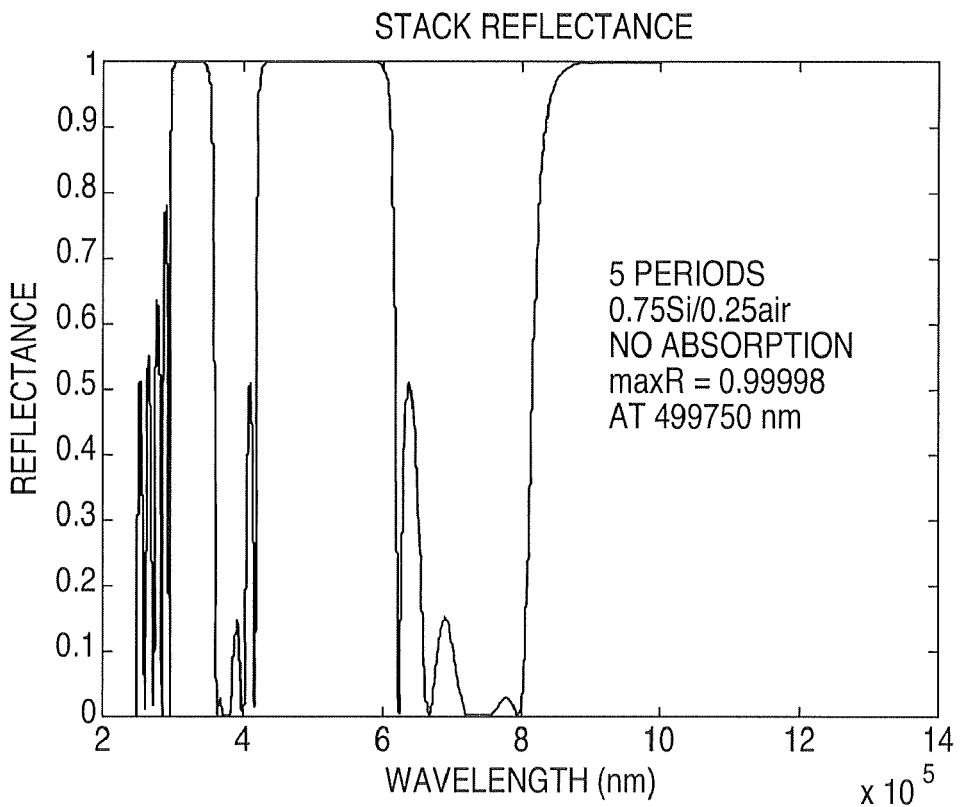

FIGS. 11A and 11B illustrate graphs of example reflectances of a terahertz mirror according to this disclosure. In particular, FIG. 11A illustrates a graph of the reflectance of the mirror 1000 that includes a quarter-wave silicon film and a quarter-wave air layer. FIG. 11B illustrates a graph of the reflectance of the mirror 1000 that includes a three-quarter-wave silicon film and a quarter-wave air layer. In these examples, no absorption value was utilized (K=0), and both embodiments yield a maximum reflectance ("max R") of nines to a fifth decimal place (also called "five nines reflectance").

In particular embodiments, the mirror 1000 can be manufactured using MEMS processing. Also, each mirror period 1005, 1010, 1020, 1030, 1040 could include a basic high-index|low-index mirror period, such as high resistivity silicon (n=3.418) and air (n=1) (although any other suitable material or materials could be used).

Figure 12:
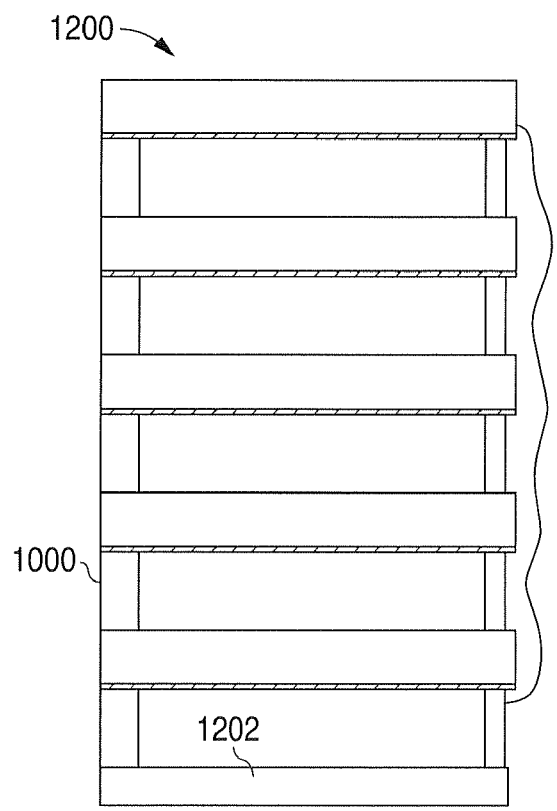
FIG. 12 illustrates another example terahertz high reflectance mirror according to this disclosure.

FIG. 12 illustrates another example terahertz high reflectance mirror 1200 according to this disclosure. The embodiment of the mirror 1200 shown in FIG. 12 is for illustration only. Other embodiments of the mirror 1200 could be used without departing from the scope of this disclosure.

In this example, the mirror 1200 includes the same general structure as the mirror 1000. In addition, the mirror 1200 includes a spacer layer 1202, which could be formed from any suitable material(s) like high quality fused silica (SiO$_2$). The spacer layer 1202 can be used to separate the period cavity within the bottom mirror period and an underlying substrate. For SiO$_2$, the value of n used could be 1.95+i0.008. In other embodiments, the spacer layer 1202 could be silicon.

Although these figures have illustrated two example terahertz high reflectance mirrors and various structures and methods for fabricating the terahertz high reflectance mirrors, various changes may be made to these figures. For example, a terahertz high reflectance mirror could include any suitable number of mirror periods. Also, a terahertz high reflectance mirror could be fabricated using any suitable structures and any suitable series of processing operations (such as photoresist patterning, etches, and sawing).

Figure 13:
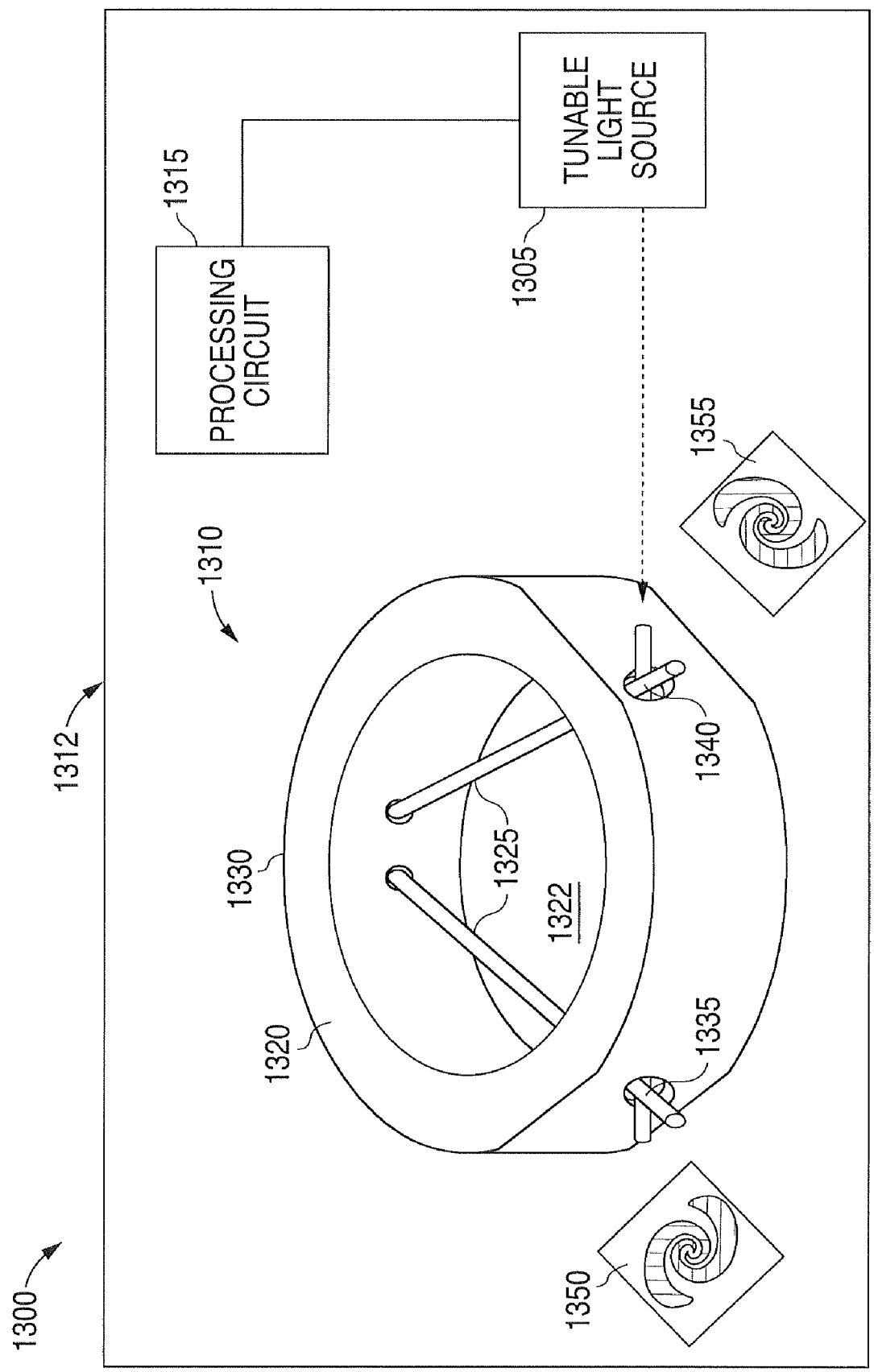
FIG. 13 illustrates an example gas detection system according to this disclosure.

FIG. 13 illustrates an example gas detection system 1300 according to this disclosure. The embodiment of the gas detection system 1300 shown in FIG. 13 is for illustration only. Other embodiments of the gas detection system 1300 could be used without departing from the scope of this disclosure.

In this example, the gas detection system 1300 includes a tunable light source 1305 and gas detection cell 1310. In some embodiments, the tunable light source 1305 and the gas detection cell 1310 are contained within a housing 1312. In other embodiments, the tunable light source 1305 and the gas detection cell 1310 are not contained within the same housing.

The tunable light source 1305 represents any suitable tunable signal source, such as a monochromatic terahertz light source. For example, the tunable light source 1305 could be operable to emit light at a wavelength between 100 GHz and 10,000 GHz. The tunable light source 1305 can also adjust the wavelength of the emitted light. In some embodiments, the tunable light source 1305 is coupled to a processing circuit 1315, which can control the tuning of the tunable light source 1305. The processing circuit 1315 could tune the light source 1305 in any suitable manner, such as in response to operator input or based on software/firmware instructions. In particular embodiments, the tunable light source 1305 represents a backward wave oscillator ("BWO"). The processing circuit 1315 includes any suitable processing or computing device for controlling a tunable light source.

In this example, the gas detection cell 1310 includes a resonant cavity 1320, which includes a gas chamber 1322. The gas chamber 1322 is an area containing a gas or gases. The light emitted by the tunable light source 1305 traverses an absorption path through the gas chamber 1322. As the light traverses the absorption path through the gas chamber 1322, portions of light energy are absorbed by the gas or gases present in the gas chamber 1322.

The gas detection cell 1310 also includes at least one high reflectance terahertz mirror 1330 (located on the far side of the resonant cavity 1320 in FIG. 13). The high reflectance terahertz mirror 1330 could, for example, represent a mirror as shown in FIG. 10 or FIG. 12 and described above. The gas detection cell 1310 further includes a first terahertz detector 1350 and a second terahertz detector 1355.

In some embodiments, the high reflectance terahertz mirror 1330 is mounted on a piezo-transducer and a position actuator. The terahertz mirror 1330 can also be coupled to the processing circuit 1315. The actuator for the terahertz mirror 1330 can be controlled by the processing circuit 1315 to vary an angle of incidence of reflected light. This can be done to adjust the absorption path length of the cavity resonance based on the frequency of the light emitted from the tunable light source 1305. The processing circuit 1315 can therefore tune the resonant cavity 1320 by varying the angle of incidence of the terahertz mirror 1330, such as by varying the angle of incidence so that a Fabry-Perot resonance is achieved. The processing circuit 1315 can also tune the resonant cavity 1320 in any suitable manner, such as based on operator input, software/firmware instructions, or signals received from the piezo-transducer.

Depending on the implementation, the gas detection cell 1310 could include a second terahertz mirror 1335 and possibly a third terahertz mirror 1340. If two terahertz mirrors 1330-1335 are used, the gas detection cell 1310 could be linear in shape. If three terahertz mirrors 1330-1340 are used, the resonant cavity 1320 can be a closed triangular absorption cavity. In embodiments where three terahertz mirrors 1330-1340 are used, each leg 1325 of the resonant cavity 1320 can be 10 cm in length to create a physical absorption path of thirty centimeters (30 cm). This could allow the gas detection cell 1310 and the tunable light source 1305 to fit within one cubic foot (1 ft$^3$). Also, in these embodiments, the processing circuit 1315 can be configured to optimize the gas detection system 1300, such as by tuning the resonant cavity 1320 by varying the angle of incidence of the terahertz mirror 1330 based on the frequency of the light source 1305 until a Fabry-Perot resonance is achieved within the resonant cavity 1320.

The use of the terahertz mirrors 1330-1340, which can have a reflectance greater than 0.999 in the gas detection cell 1310, can effectively increase the absorption path length by a large amount. As a particular example, the absorption path length could be increased by approximately one thousand times, such as by increasing the absorption path length from 0.5 m to 1000 m. Accordingly, the gas detection system 1300 can be quite compact and achieve a high sensitivity (such as parts per billion) in a small volume.

In this example, the first terahertz detector 1350 is configured to detect a transmitted signal from the tunable light source 1305. The second terahertz detector 1355 is configured to detect a reflected signal from one or more of the terahertz mirrors 1330-1340. The terahertz detectors 1350-1355 may represent uncooled, high sensitivity detectors, and each can include a MEMS microbridge with a noise equivalent power less than 10 pW/$\sqrt{\text{Hz}}$ (NEP<10 pW/$\sqrt{\text{Hz}}$) and a 100 μs response. In some embodiments, the terahertz detectors 1350-1355 could each include a Schottky-barrier diode with a 1 ns response for cavity ring-down spectroscopy methods.

Note that the embodiment of the gas detection cell 1310 shown in FIG. 13 is for illustration only. Other embodiments of the gas detection cell 1310 could be used. In particular, one or more terahertz mirrors could be used in any suitable gas detection cell.

FIGS. 14A through 14F illustrate example absorption peaks of gases of interests according to this disclosure. The gases shown here are for illustration only. Other gases with their associated absorption peaks could also be detected.

Figure 14A:
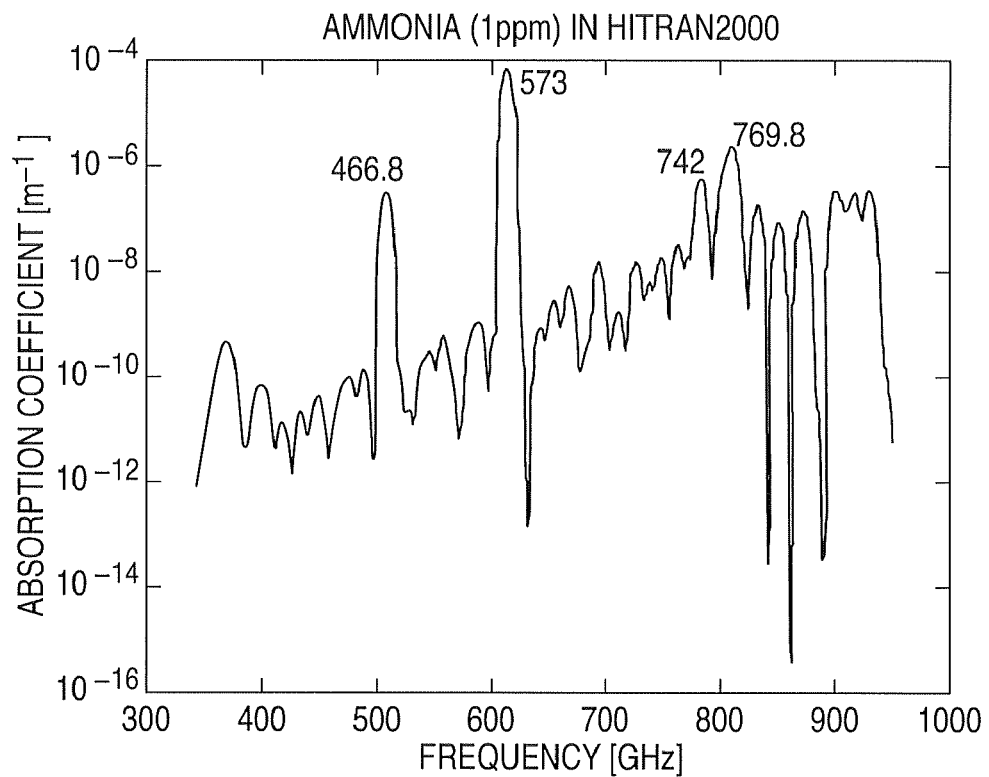
FIGS. 14A through 14F illustrate example absorption peaks of gases of interests according to this disclosure.
Figure 14B:
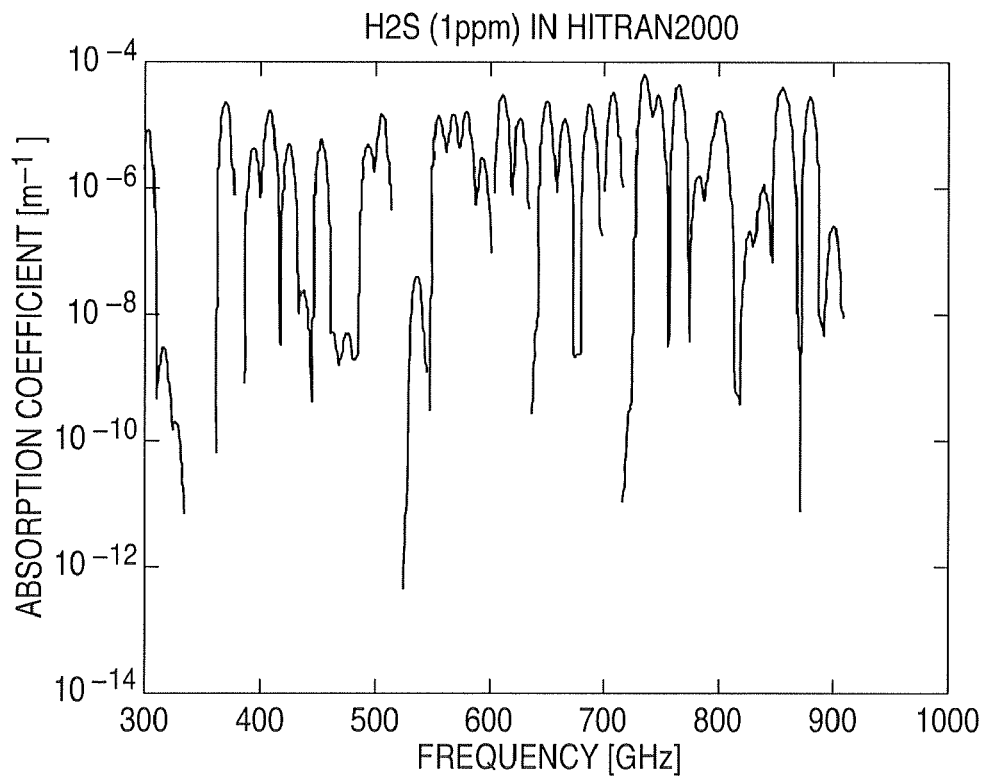
Figure 14C:
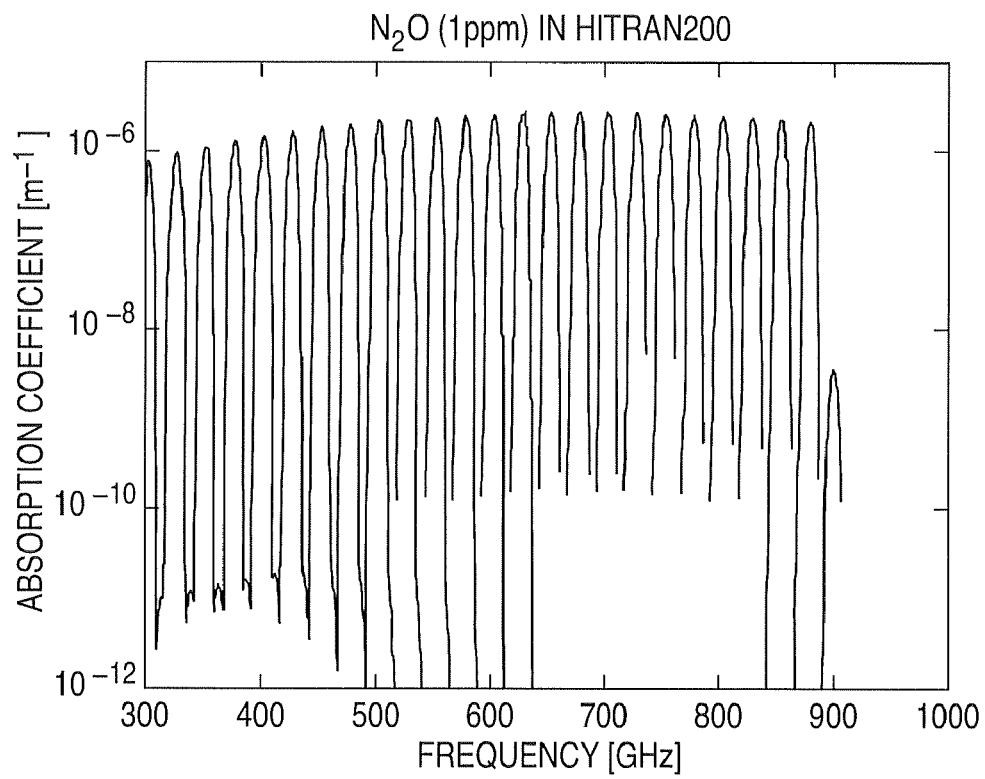
Figure 14D:
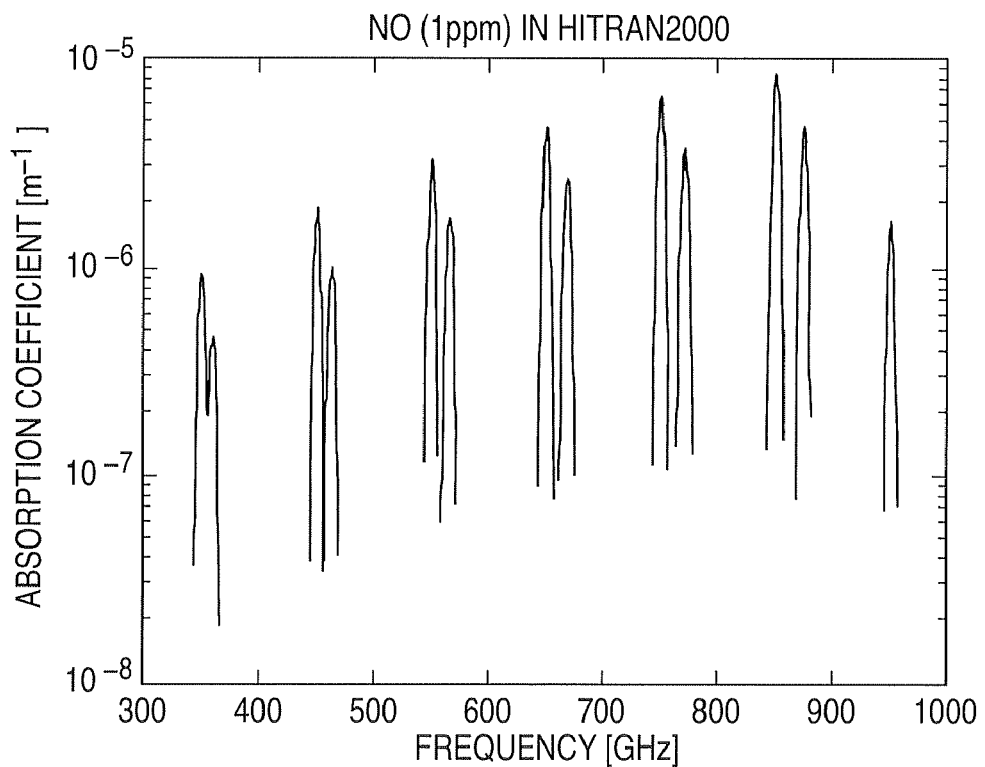
Figure 14E:
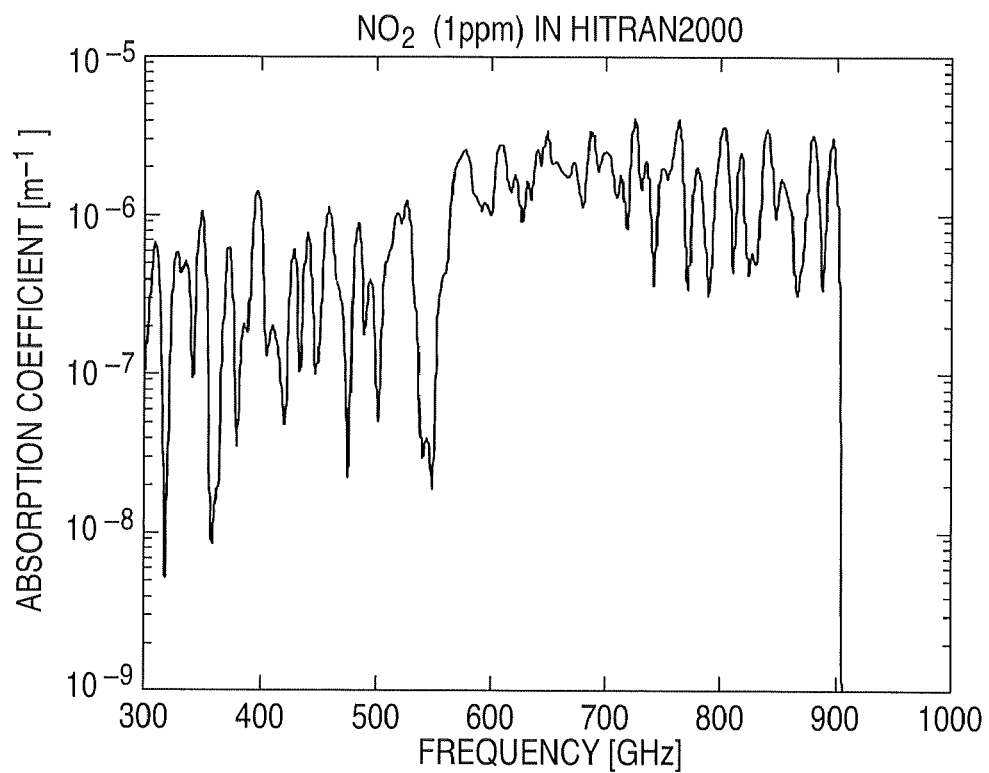
Figure 14F:
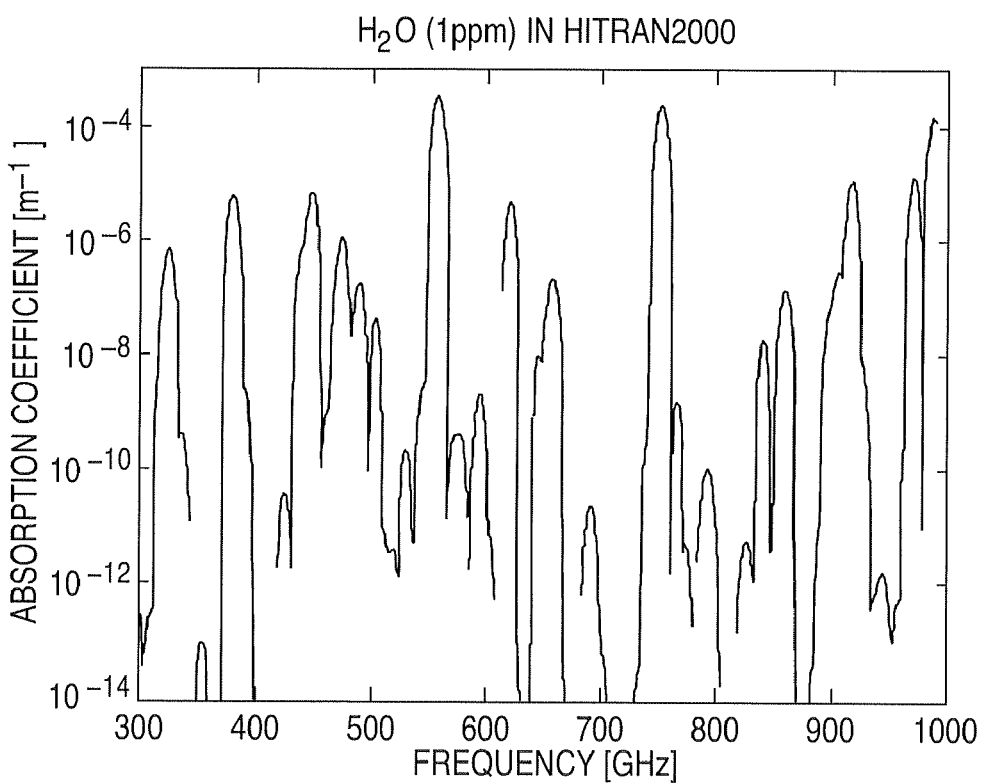

FIG. 14A illustrates the absorption peaks of ammonia.
FIG. 14B illustrates the absorption peaks of hydrogen sulfide.
FIG. 14C illustrates the absorption peaks of nitrous oxide.
FIG. 14D illustrates the absorption peaks of nitrogen oxide.
FIG. 14E illustrates the absorption peaks of nitrogen dioxide.
FIG. 14F illustrates the absorption peaks of water. Absorption peaks, as illustrated in FIGS. 14A through 14F, are typically unique to gases of interest.

These absorption peaks can be used by the gas detection system 1300 to determine if any of these gases are present in a sample. For example, the gas detection system 1300 can compare the transmitted signal detected by the first detector 1350 (the signal transmitted from the light source 1305) to the signal detected by the second detector 1355 (the reflected signal). The gas detection system 1300 can use this to determine an absorption of the light signal based on the comparison of the transmitted and reflected signals. The gas detection system 1300 can then identify the gas or gases present based on the absorption of the light signal at the frequency or frequencies generated by the light source 1305. Accordingly, the gas detection system 1300 is operable to determine the presence of a gas within the gas detection cell 1310.

Figure 15:
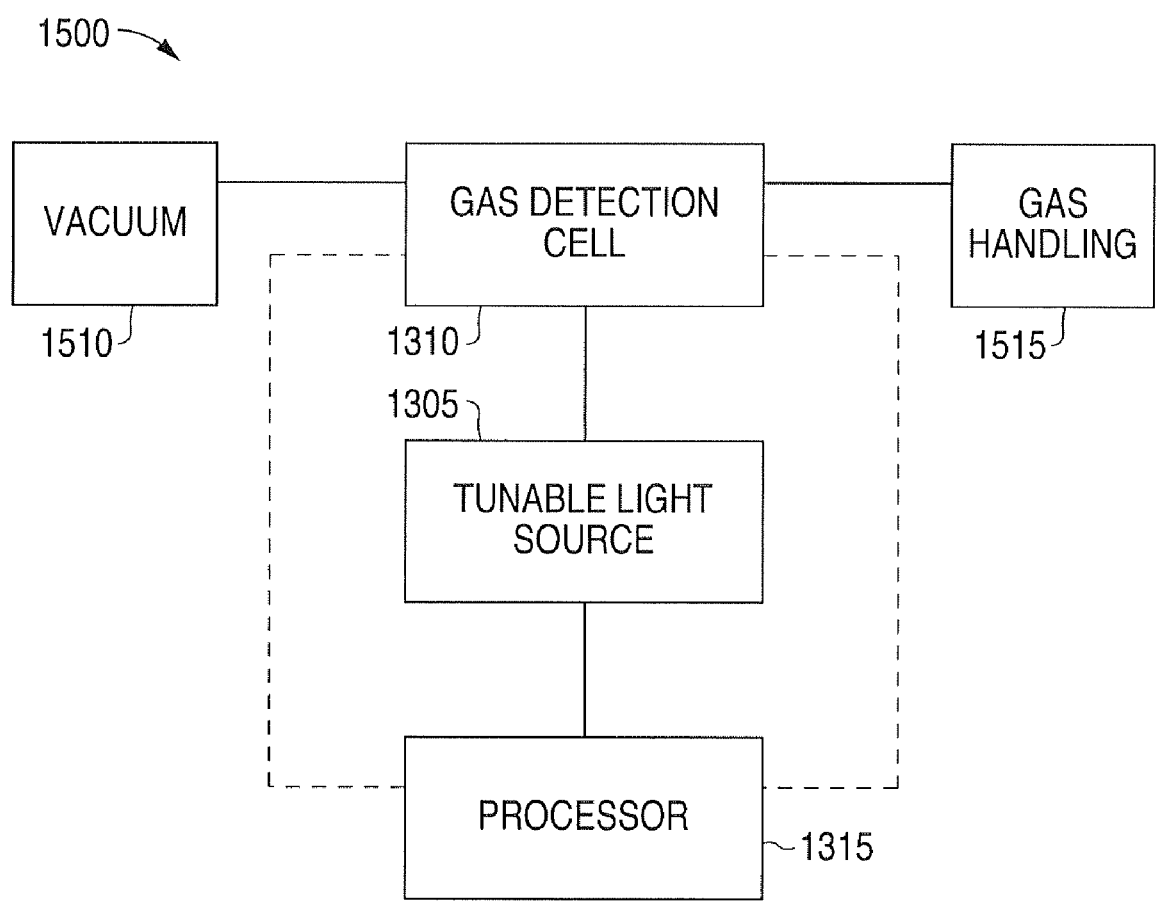
FIG. 15 illustrates another example gas detection system according to this disclosure.

FIG. 15 illustrates another example gas detection system 1500 according to this disclosure. The embodiment of the gas detection system 1500 shown in FIG. 15 is for illustration only. Other embodiments of the gas detection system 1500 could be used without departing from the scope of this disclosure.

In this example, the gas detection system 1500 includes the same general structure as the gas detection system 1300. In addition, to eliminate possible overlap of absorption peaks of certain gases due to pressure broadening, the gas detection system 1500 can operate at reduced pressure, such as between one thousandth to one hundredth of an atmosphere ($10^{-3}$ to $10^{-4}$ atmosphere). The gas detection system 1500 is coupled to vacuum equipment 1510 and gas handling equipment 1515. The vacuum equipment 1510 is operable to reduce a pressure in the gas detection cell 1310, and the gas handling equipment 1515 is operable to introduce gas to be measured into the gas detection cell 1310.

Although these figures have illustrated two example gas detection systems and various absorption peaks detected, various changes may be made to these figures. For example, the gas detection cell could have any suitable configuration, such as linear or pentagonal, and can include any number of high reflectance terahertz mirrors. Also, more than one high reflectance terahertz mirror may be mounted on a position actuator. In these embodiments, the processing circuit 1315 can tune the resonant cavity 1320 by varying the angle of incidence of one or more of the terahertz mirrors. In addition, the tunable light source 1305 could represent a laser, such as a gas laser, or any other suitable tunable light source.

It may be advantageous to set forth definitions of certain words and phrases used throughout this patent document. The term "couple" and its derivatives refer to any direct or indirect communication between two or more elements, whether or not those elements are in physical contact with one another. The terms "include" and "comprise," as well as derivatives thereof, mean inclusion without limitation. The term "or" is inclusive, meaning and/or. The phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like.

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure, as defined by the following claims.

What is claimed is:

1. An apparatus comprising:
a resonant cavity configured to receive a light signal;
a first detector configured to measure the light signal;
two or more high reflectance terahertz mirrors configured to reflect the light signal within the resonant cavity such that the reflected light signal traverses multiple paths through a gas present in the resonant cavity, each terahertz mirror comprising a plurality of periods arranged in a stack, each period comprising a semiconductor layer and a dielectric film, wherein the semiconductor layer of each period is separated from the dielectric film of an adjacent period by a period cavity; and
a second detector configured to measure the reflected light signal.

2. The apparatus of claim 1, wherein at least one of the two or more high reflectance terahertz mirrors is mounted on a position actuator.

3. The apparatus of claim 2, wherein the position actuator is configured to adjust a position of the at least one high reflectance terahertz mirror to adjust a resonance of the reflected light signal within the resonant cavity.

4. The apparatus of claim 3, further comprising:
a processing circuit configured to adjust the resonance of the reflected light signal based on a frequency of the light signal to obtain a Fabry-Perot resonance.

5. The apparatus of claim 1, wherein the resonant cavity is a closed triangular absorption cavity.

6. The apparatus of claim 5, wherein the apparatus comprises three high reflectance terahertz mirrors.

7. The apparatus of claim 1, wherein each high reflectance terahertz mirror comprises a five-period silicon-air mirror.

8. The apparatus of claim 1, wherein a length of each path through the resonant cavity is approximately 10 centimeters.

9. The apparatus of claim 1, wherein:
the semiconductor layer of each period has a thickness in a range of approximately 37 µm to 115 µm;
the dielectric film of each period has a thickness of approximately 0.5 µm; and
each period cavity has a thickness in a range of approximately 120 µm to 130 µm.

10. A system comprising:
a tunable light source configured to emit a light signal at an adjustable wavelength; and
a gas detection cell comprising:
a resonant cavity configured to receive the light signal;
a first detector configured to measure the light signal;
two or more high reflectance terahertz mirrors configured to reflect the light signal within the resonant cavity such that the reflected light signal traverses multiple paths through a gas present in the resonant cavity, each terahertz minor comprising a plurality of periods arranged in a stack, each period comprising a semiconductor layer and a dielectric film, wherein the semiconductor layer of each period is separated from the dielectric film of an adjacent period by a period cavity; and
a second detector configured to measure the reflected light signal.

11. The system of claim 10, wherein at least one of the two or more high reflectance terahertz mirrors is mounted on a position actuator, the position actuator operable to adjust an angle of incidence of the at least one high reflectance terahertz mirror.

12. The system of claim 11, further comprising a processing circuit configured to:
tune the tunable light source to a specified frequency; and
adjust the angle of incidence of the at least one high reflectance terahertz minor such that a Fabry-Perot resonance of the light signal is obtained in the resonant cavity.

13. The system of claim 10, wherein the resonant cavity is a closed triangular absorption cavity.

14. The system of claim 13, wherein a length of each path through the resonant cavity is approximately 10 centimeters.

15. The system of claim 10, wherein the gas detection cell comprises multiple high reflectance terahertz mirrors.

16. The system of claim 10, wherein:
the tunable light source is configured to emit a light signal having a wavelength in a range between 100 GHz and 10,000 GHz inclusive; and
the two or more high reflectance terahertz mirrors are configured to reflect a reflected light signal having a wavelength in a range between 100 GHz and 10,000 GHz inclusive.

17. A method comprising:
receiving a light signal;
measuring the light signal;
reflecting the light signal using at least one high reflectance terahertz mirror such that a distance traveled by the light signal is substantially increased, the at least one high reflectance mirror comprising a reflectance greater than 0.999 at a wavelength in a range of 100 GHz and 10,000 Ghz, the at least one high reflectance mirror comprising a plurality of periods arranged in a stack, each period comprising a semiconductor layer and a dielectric film, wherein the semiconductor layer of each period is separated from the dielectric film of an adjacent period by a period cavity;
measuring the reflected light signal;
comparing the light signal and the reflected signal;
identifying an absorption of the light signal; and
determining a presence of a gas based on the identified absorption of the light signal at one or more specified frequencies.

18. The method of claim 17, further comprising generating the light signal by a tunable light emission source.

19. The method of claim 18, further comprising adjusting an angle of incidence of the at least one high reflectance terahertz mirror to obtain a Fabry-Perot resonance of the light signal.

20. The method of claim 18, further comprising reflecting the reflected light signal by a second high reflectance terahertz mirror.

21. The method of claim 20, further comprising reflecting the reflected light signal by a third high reflectance terahertz mirror.

* * * * *